United States Patent [19]

Berthold et al.

[11] 4,169,851

[45] Oct. 2, 1979

[54] PROCESS FOR THE MANUFACTURE OF ACETOACETYL-AMINOBENZENES

[75] Inventors: Rüdiger Berthold, Bad Soden am Taunus; Wolfgang Tronich, Hofheim am Taunus, both of Fed. Rep. of Germany

[73] Assignee: Hoechst Aktiengesellschaft, Frankfurt am Main, Fed. Rep. of Germany

[21] Appl. No.: 957,041

[22] Filed: Nov. 2, 1978

[30] Foreign Application Priority Data

Nov. 4, 1977 [DE] Fed. Rep. of Germany ....... 2749327

[51] Int. Cl.$^2$ ............................................ C07C 102/00
[52] U.S. Cl. ................................................ 260/562 K
[58] Field of Search ......................... 260/562 K, 561 K

[56] References Cited

U.S. PATENT DOCUMENTS

| | | |
|---|---|---|
| 2,542,565 | 2/1951 | Parker ............................... 260/526 K |
| 2,714,117 | 7/1955 | Lacey ............................... 260/562 K |
| 3,121,743 | 2/1964 | Branch ............................. 260/562 K |
| 3,304,328 | 2/1967 | Pelley ............................... 260/562 K |
| 3,778,474 | 12/1973 | Stocker ............................ 260/561 K |
| 4,042,622 | 8/1977 | Casithory et al. ............... 260/562 K |

FOREIGN PATENT DOCUMENTS 2519036 11/1976 Fed. Rep. of Germany .

*Primary Examiner*—Arthur P. Demers
*Attorney, Agent, or Firm*—Curtis, Morris & Safford

[57] ABSTRACT

The N-acetoacetylamino compounds of 2,5-dimethoxy-4-chloro-aniline, 2,4-dimethyl-aniline and 2-methyl-5-chloroaniline are obtained in a good yield and excellent purity, if the above-mentioned anilines are reacted with diketene in an inert organic solvent or diluent in the presence of from 0.1 to 6%, calculated on the weight of the aniline, of water, while adding catalytic amounts of acid. An industrial aniline quality is preferably dried by heating it with a solvent forming with water an azeotropic mixture, and thereafter the amount of water required is added. The products may be used without purification as coupling components for the preparation of pigments.

6 Claims, No Drawings

PROCESS FOR THE MANUFACTURE OF ACETOACETYL-AMINOBENZENES

The present invention relates to a process for the manufacture of acetoacetyl-aminobenzenes.

From German Pat. No. 2,518,984 there is known a process for the manufacture of N-acetoacetyl-2,5-dimethoxy-4-chloroanilide, in which 2,5-dimethoxy-4-chloro-aniline is suspended in water and reacted with diketene, the diketene being added at once right at the start of the reaction. In this reaction there are preferably added inorganic or especially organic acids, advantageously from 0.1 to 1 mol of acid per mol of aniline.

From German Offenlegungsschrift No. 25 19 036 it is known to manufacture acetoacetyl-arylamides by reacting primary aromatic amines with diketene in water in a manner that the reaction is carried out at a temperature, at which the product of the process is not present in the solid state. This reaction is preferably executed in aqueous acetic acid of a concentration of up to about 60% by weight.

From British Pat. No. 962,227 it is known to manufacture acetoacetyl-arylamides by reacting the arylamines with diketene in toluene, while adding tertiary amines as catalysts.

It has now been found that with three specially substituted anilines the reaction proceeds in a particularly favorable manner and yields products of high purity, if as reaction medium there is used an inert organic solvent, and if besides the catalytic amounts of acid there are also present catalytic amounts of water.

Thus, the subject of the present invention is a process for the manufacture of 1-acetoacetylamino-2,5-dimethoxy-4-chlorobenzene, 1-acetoacetylamino-2,4-dimethylbenzene and 1-acetoacetylamino-2-methyl-5-chlorobenzene from diketene and the corresponding aniline in the presence of water with the addition of catalytic amounts of acid, which comprises reacting the aniline in an inert organic solvent or diluent in the presence of from 0.1 to 6% of water, calculated on the weight of the aniline.

The amount of water is preferably of from 0.1 to 3%, especially from 0.15 to 0.35%. Preferred solvents or diluents are hydrocarbons, such as petroleum ether, cyclohexane, benzene, toluene, xylene or industrial mixtures of these solvents, as they are sold, for example, under the trade name of "Solventnaphtha." However, use may also be made of inert chlorinated hydrocarbons, such as chlorinated aromatic compounds. Particularly when using moist industrial-grade amines, there are preferably used solvents and diluents which form an azeotropic mixture with water, such as toluene or xylene, thus allowing a simple elimination of the water prior to the reaction with the diketene. Therefore, a preferred embodiment is to be seen in the process of drying the amine with such a solvent forming an azeotropic mixture and subsequently adding the amount of water desired. It is also possible, however, to use industrial-grade aniline which contains only a small amount of water, and to adjust the concentration of water according to the invention thereafter.

An amount of water larger than that according to the invention lead to a loss in quality of the product and requires a working-up of the waste obtained.

As an acid showing a catalytic action there is preferably added an organic acid. There may be mentioned low molecular weight mono- and polycarboxylic acids which may also be substituted by groups being inert towards the amine, for example hydroxy groups. Preference is given to lower alkane carboxylic acids, especially acetic acid, since industrial diketene contains acetanhydride anyhow. Generally, there is added up to about 0.5 mol of acid per mol of amine; larger amounts of acid are possible, but they do not result in a higher yield.

The reaction temperature should not exceed 10° C. at the beginning. In order to keep the cooling expenditure as low as possible with favorable reaction times, the diketene is added suitably portionwise or continuously, optionally with interruptions. The diketene is suitably used in a small excess amount of up to about 10%. A larger excess of diketene may lead to a quality loss of the product.

During the addition of the diketene, the temperature of the reaction mixture may be allowed to rise to a level above room temperature and the reaction may subsequently be completed by after-stirring.

The reaction products are obtained in a crystalline form. In order to isolate the product, the reaction mixture is suitably cooled, preferably to a temperature in the range of from about −10° to −5° C. By concentrating the mother liquor, a further fraction may be obtained.

In the process of the invention there is practically not obtained any waste water. The solvent and/or diluent is recovered by distillation, which requires far less energy than distilling off water. The resin-like distillation residue can be incinerated.

The following Examples serve to illustrate the invention, the percentages being by weight.

EXAMPLE 1

232.6 g of moist industrial-grade 2,5-dimethoxy-4-chloroaniline with a purity of 80.6% (corresponding to 187.5 g of 100% purity = 1 mol) are boiled with 700 ml of toluene, until no more water is separated at a water separator. After cooling, g of formic acid (100% strength) and g of water are added, and within about 30 minutes g of diketene (1.1 mol) are introduced while stirring in a manner that the temperature does not exceed 50° C. Stirring is continued for another hour without cooling, and thereafter g of charcoal and g of kieselguhr are added, and the reaction solution is clarified at about 100° C. After cooling to room temperature the mixture is cooled for 2 hours with brine to a temperature in the range of from −8° to −5° C. in order to complete the precipitation, and the precipitated product is filtered off with suction. After drying, 233.5 g of 1-acetoacetylamino-2,5-dimethoxy-4-chlorobenzene are obtained (86% of the theory). The mother liquor is concentrated to about one third, in which process there are obtained another 16.3 g of the product (=6% of the theory).

The product is obtained in excellent purity. When extracting a sample with methanol, practically no amine can be detected any more in the extract. The product is excellently suitable as coupling component for the preparation of pigments.

The reactions with 2,4-dimethyl-aniline and 2-methyl-5-chloro-aniline are carried out analogously.

Instead of formic acid, there may also be employed propionic acid and especially acetic acid with the same result.

EXAMPLE 2

121 g of distilled 2,4-dimethylaniline (purity degree 99.9% =0.1 mol) are mixed with
700 ml of anhydrous toluene, and
25 g of anhydrous acetic acid are added. Then there are added, while stirring,
0.3 ml of water and, within 30 minutes without cooling,
92 g of diketene (1.1 mol).

In the course of this process the temperature rises gradually to 50° C. Stirring is continued for one hour, and subsequently
5 g of charcoal and
5 g of kieselguhr are added, and the reaction solution is clarified at about 100° C. Subsequently the mixture is cooled to room temperature (about 20° C.), and the precipitation is completed by cooling for 2 hours with brine to a temperature in the range of from −8° to −5° C. The precipitated product is filtered off with suction, dried, and as a result there are obtained
165 g of 1-acetoacetylamino-2,4-dimethylbenzene (80% of the theory). The mother liquor is concentrated to about one third, in which process there are obtained another
14.5 g of the product (=7% of the theory).

What is claimed is:
1. Process for the manufacture of 1-acetoacetylamino-2,5-dimethoxy-4-chlorobenzene, 1-acetoacetylamino-2,4-dimethylbenzene and 1-acetoacetylamino-2-methyl-5-chlorobenzene from diketene and the corresponding aniline in the presence of water with the addition of catalytic amounts of acid, which comprises reacting the aniline in an inert organic solvent or diluent in the presence of from 0.1 to 6%, calculated on the weight of the aniline, of water.

2. A process as claimed in claim 1, wherein the amount of water is in the range of from 0.1 to 3%.

3. A process as claimed in claim 1, wherein the amount of water is in the range of from 0.15 to 0.35%.

4. A process as claimed in claim 1, wherein the inert solvent or diluent is a substance which forms with water an azeotropic mixture.

5. A process as claimed in claim 1, wherein the inert solvent or diluent is toluene or xylene.

6. A process as claimed in claim 1, which comprises drying a water-containing aniline in situ by heating it with an inert organic solvent or diluent which forms with water an azeotropic mixture, and adding the amount of water required.

* * * * *